US00PP20949P3

(12) United States Plant Patent
Sugimoto

(10) Patent No.: US PP20,949 P3
(45) Date of Patent: Apr. 27, 2010

(54) *ASPLENIUM* PLANT NAMED 'CRISPY WAVE'

(50) Latin Name: *Asplenium nidus*
Varietal Denomination: CRISPY WAVE

(75) Inventor: Yuki Sugimoto, Fukuoka (JP)

(73) Assignee: Shinryuen Sugimoto, Yamato-Gun, Fukuoka (JP)

( * ) Notice: Subject to any disclaimer, the term of this patent is extended or adjusted under 35 U.S.C. 154(b) by 215 days.

(21) Appl. No.: 11/812,119

(22) Filed: Jun. 15, 2007

(65) Prior Publication Data

US 2007/0245440 P1 Oct. 18, 2007

(51) Int. Cl.
*A01H 5/00* (2006.01)

(52) U.S. Cl. ..... Plt./379

(58) Field of Classification Search ..... Plt./379
See application file for complete search history.

(56) References Cited

OTHER PUBLICATIONS

Print out for corresponding, international PBR application, CPVO 2005/1683 filed Oct. 7, 2005 from EU-CPVO web site (http://www.cpvoextranet.cpvo.europa.eu/WD100AWP/WD100Awp.exe/CTX_696-7-rOMLKOYASY/frmTable_File/SYNC_-1706817687?A25 ) (3 pages).

*Primary Examiner*—Kent L Bell
(74) *Attorney, Agent, or Firm*—Foley & Lardner LLP

(57) ABSTRACT

A new distinct cultivar of *Asplenium* plant named 'CRISPY WAVE', characterized by its lanceolate-shaped fronds, which are extremely stiff and curvy; fronds color ranges from RHS 146A to RHS 147C; and plants are dense and bushy in plant form.

3 Drawing Sheets

Latin name of the genus and species of the claimed plant: *Asplenium nidus*.

Variety denomination: 'CRISPY WAVE'.

BACKGROUND OF THE INVENTION

The present invention relates to a new and distinct cultivar of *Asplenium* plant, botanically known as *Asplenium nidus L.*, of the Aspleniaceae, commonly known as Birds Nest Fern, and hereinafter referred to by the variety denomination 'CRISPY WAVE'.

The new *Asplenium* 'CRISPY WAVE' is a product of a planned breeding program conducted in Yaku Island, Kagoshima Prefecture, Japan. A naturally occurring whole plant mutation of the unpatented *Asplenium nidus L.* 'OSAKA' was discovered and selected as a single flowering plant by the inventor's grandfather, Haruo Sugimoto, in 1961. Many more years of spore propagation and further selection in the proprietary offspring of 'OSAKA' resulted in the discovery and selection of the new *Asplenium* 'CRISPY WAVE' in 2000 by the inventor, Yuki Sugimoto. The parent plant of 'CRISPY WAVE' is an unnamed, unpatented proprietary *Asplenium nidus L.* plant, and is an offspring of 'OSAKA'. Plants of the new *Asplenium* 'CRISPY WAVE' are more stiff, upright, and compact than plants of 'OSAKA'.

Asexual reproduction of the new *Asplenium* 'CRISPY WAVE' cultivar by spores was first performed by the inventor, Yuki Sugimoto, in 2000 in Yamato-gun, Fukuoka, Japan, and has demonstrated that the combination of characteristics as herein disclosed for the new cultivar are firmly fixed and retained through successive generations of spore reproduction. The new cultivar reproduces true-to-type.

SUMMARY OF THE INVENTION

The following traits have been repeatedly observed and are determined to be the unique characteristics of 'CRISPY WAVE' which in combination distinguish this *Asplenium* as a new and distinct cultivar:

1. Lanceolate-shaped fronds are extremely stiff and curvy;
2. Fronds color ranges from RHS 146A to RHS 147C; and
3. Dense and bushy plant form.

No plants of the parent plant of 'CRISPY WAVE' (an unnamed, unpatented proprietary *Asplenium nidus L.* which is an offspring of 'OSAKA') are available to provide a comparison description to plants of the new *Asplenium* 'CRISPY WAVE'. However, a comparison description is provided below of plants of the related, unpatented cultivar, *Asplenium nidus L.* 'OSAKA', to plants of the new *Asplenium nidus L.* 'CRISPY WAVE'.

Side-by-side comparisons were conducted in Fyn, Denmark, during the winter and spring seasons of 2005 to 2006, between plants of the new *Asplenium nidus L.* 'CRISPY WAVE' and the unpatented, related cultivar, *Asplenium nidus L.* 'OSAKA'. Plants of new *Asplenium nidus L.* 'CRISPY WAVE' differ from plants of the unpatented, related cultivar, *Asplenium nidus L.* 'OSAKA', in the following characteristics:

1. Plants of the new *Asplenium* 'CRISPY WAVE' produce strikingly stiff and curvy fronds whereas plants of 'OSAKA' produce soft, overhanging fronds.
2. Plants of the new *Asplenium* 'CRISPY WAVE' produce about 35 fronds, yellow-green in color (ranges from RHS 146A to RHS 147C) whereas plants of 'OSAKA' produce about 40 fronds, which are lighter yellow-green in color (RHS 146C).

3. Plants of the new *Asplenium* 'CRISPY WAVE' produce fronds with acuminate tips and truncate bases whereas plants of 'OSAKA' produces fronds with cirrose tips and tapering, attenuate bases.
4. Plants of the new *Asplenium* 'CRISPY WAVE' are more compact (height about 20 cm and spread about 26 cm) than the upright, overhanging plants of 'OSAKA' (height about 30 cm and spread ranging from 41 to 45 cm).

Of the many commercial cultivars known to the present inventor, the most similar in comparison to the new *Asplenium* 'CRISPY WAVE', is the unpatented related cultivar, *Asplenium nidus L.* 'OSAKA', as described above.

BRIEF DESCRIPTION OF THE PHOTOGRAPHS

The accompanying colored photographs illustrate the overall appearance and details of the new *Asplenium* 'CRISPY WAVE', showing the colors as true as is reasonably possible with colored reproductions of this type. Colors in the photographs may differ slightly from the color values cited in the detailed botanical description, which accurately describe the colors of 'CRISPY WAVE'.

DETAILED BOTANICAL DESCRIPTION

Figure 1:
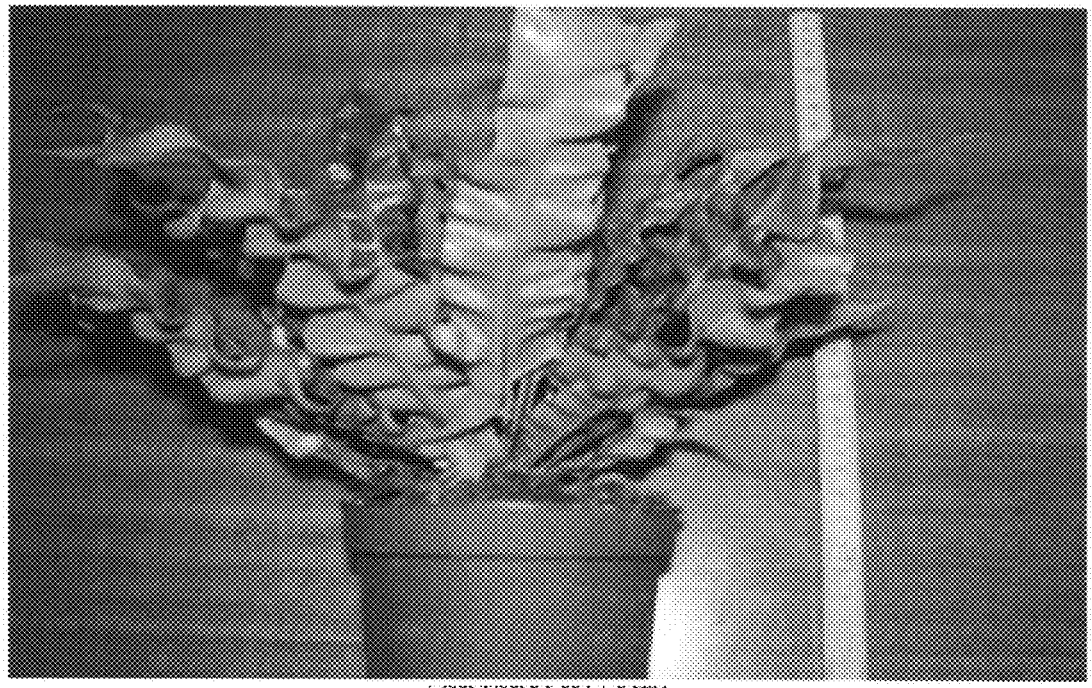
FIG. 1 shows a comparison of a side view perspective of a typical plant of the instant plant 'CRISPY WAVE' to a side view perspective of a typical plant of the related plant 'OSAKA', both in a 10.5 cm pot at 18 months of age.
Figure 1:
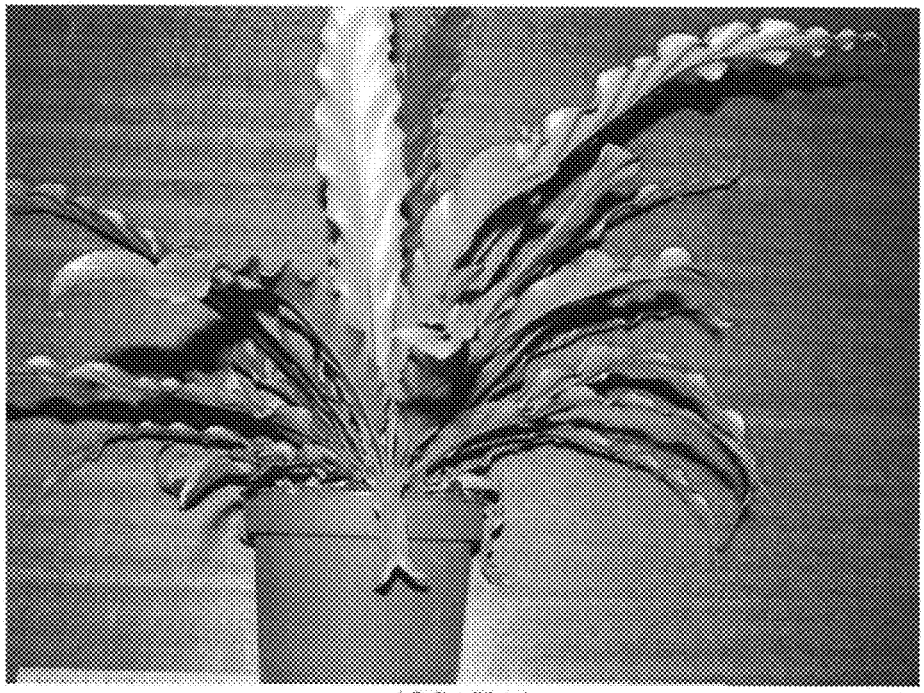
Figure 2:
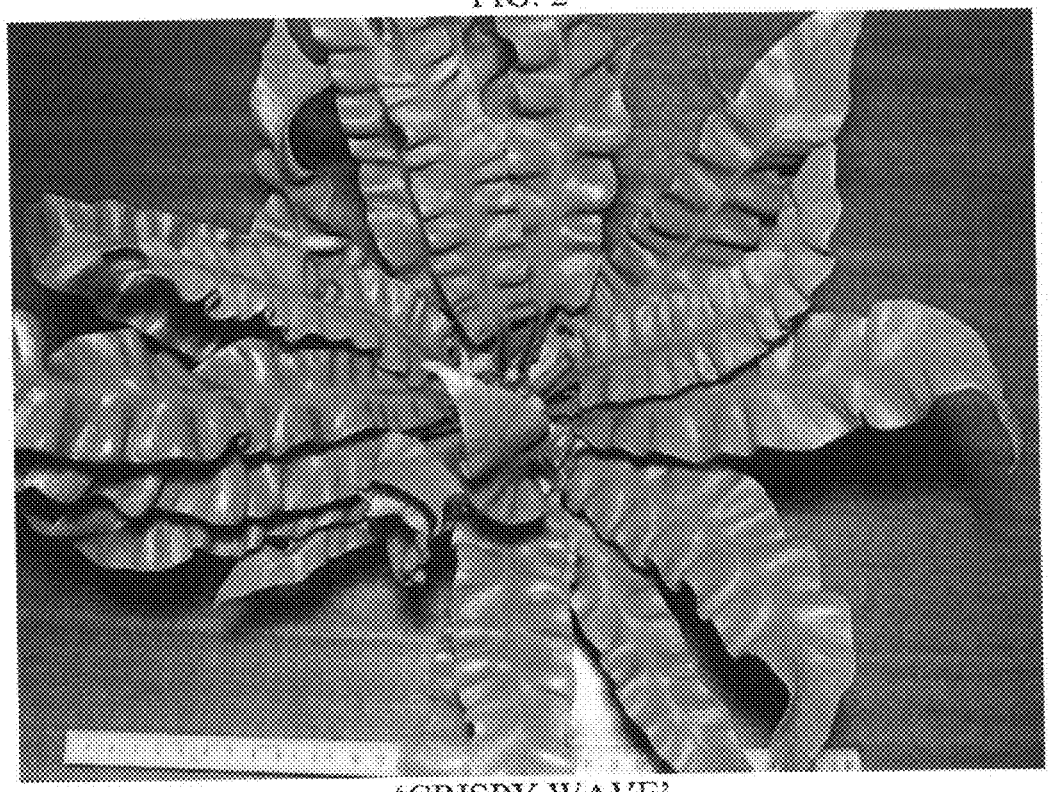
FIG. 2 shows a comparison of a top view perspective of a typical plant of the instant plant 'CRISPY WAVE' to a top view perspective of a typical plant of the related plant 'OSAKA', both in a 10.5 cm pot at 18 months of age.
Figure 2:
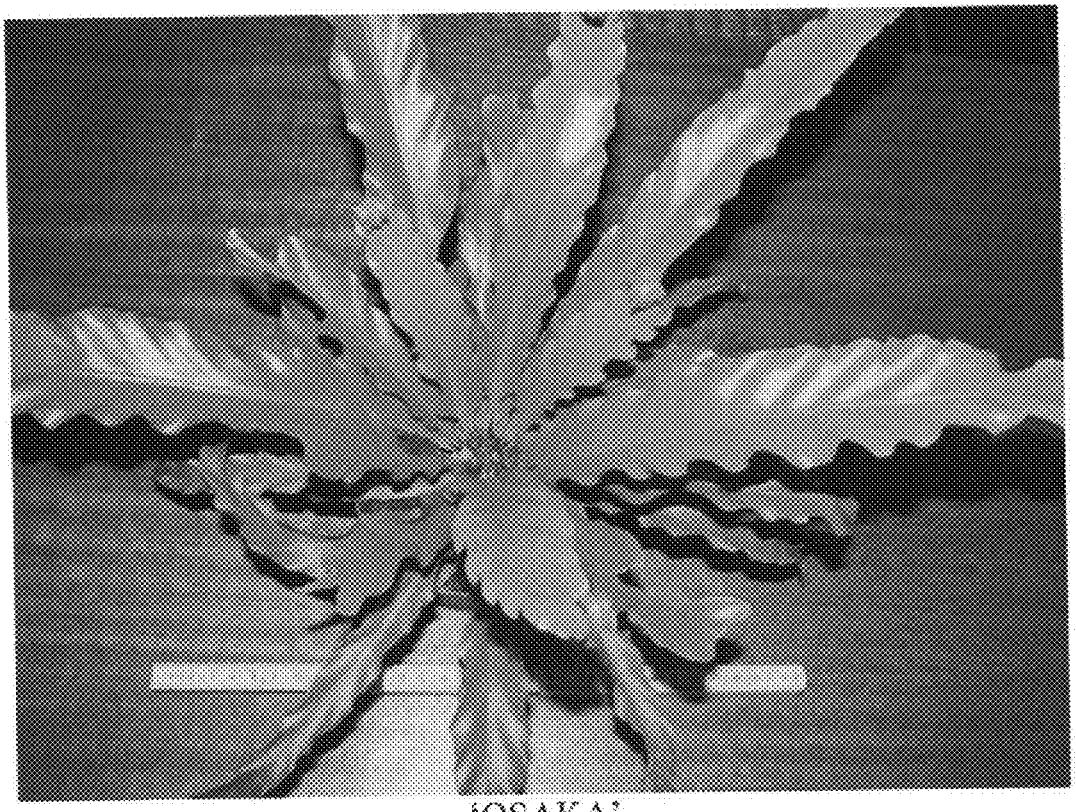
Figure 3:
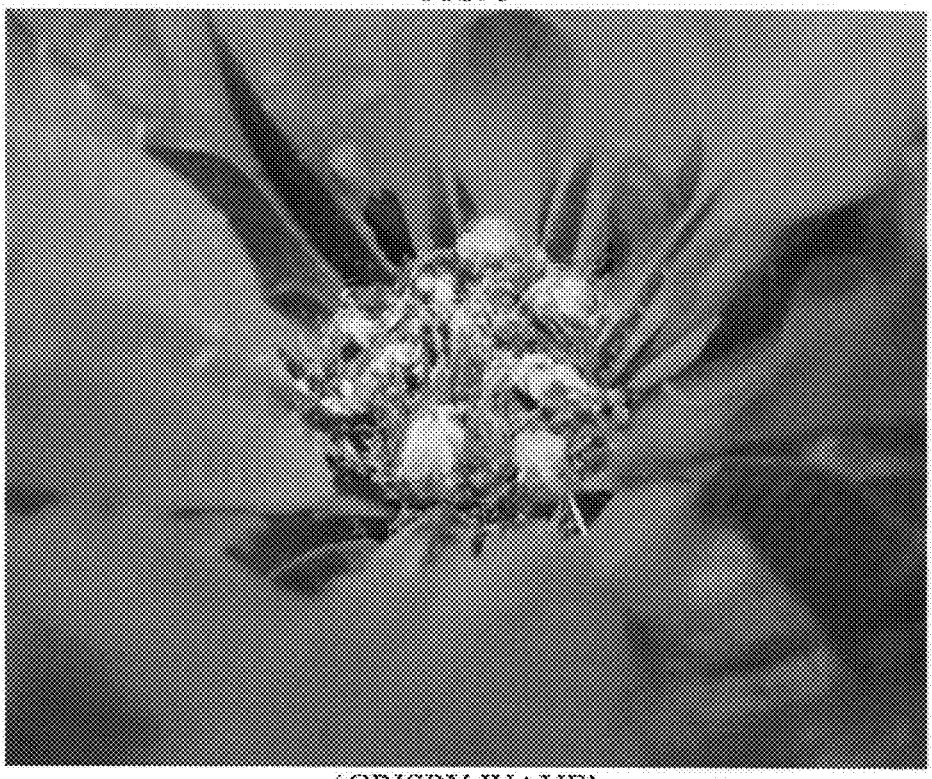
FIG. 3 shows a shows a comparison of a close-up top view perspective of a typical plant of the instant plant 'CRISPY WAVE' to a close-up top view perspective of a typical plant of the related plant 'OSAKA', both in a 10.5 cm pot at 18 months of age.
Figure 3:
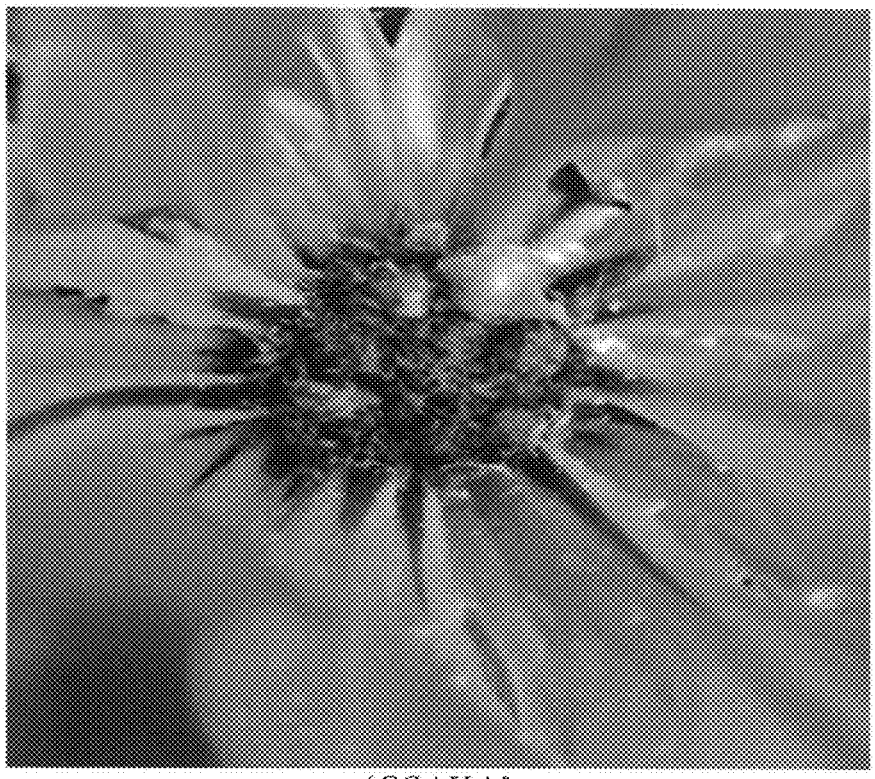

The new *Asplenium* 'CRISPY WAVE' has not been observed under all possible environmental conditions. The phenotype of the new cultivar may vary with variations in environment such as temperature, light intensity, and daylength, without any change in the genotype of the plant.

The aforementioned photographs, together with the following observations, measurements and values describe plants of the new *Asplenium* 'CRISPY WAVE' as grown in a glass-covered greenhouse in Fyn, Denmark under conditions which closely approximate those generally used in commercial practice. Plants of 'CRISPY WAVE' were grown in average day temperatures ranging from 20 to 22° C. and in an average night temperatures of 18° C. Plants of 'CRISPY WAVE' were supplemented with light for 18 hours at a light level of 40 W/m$^2$ during winter.

The photographs and descriptions were taken during the winter and spring season when outdoor day temperatures ranged from 20 to 22° C. and outdoor night temperatures averaged 18° C. The age of the plants described is 18 months after potting.

Color references are made to The Royal Horticultural Society Colour Chart (R.H.S.), 4th Edition, except where general colors of ordinary significance are used.

Botanical classification: *Asplenium nidus.*

Parentage: An unnamed, unpatented proprietary *Asplenium nidus L.* which is an offspring of the unpatented *Asplenium nidus L.* 'OSAKA'.

Propagation:

*Type.*—3 to 4 year fronds produce spores on fronds (similar to the fronds without spores). Spores are sown out on sphagnum mix in glass-covered flats. After 4 to 5 months, small prothalli emerge, and at this stage, fertilization occurs. Later sporophytes and roots emerge and the small plants can be pricked out or potted. The entire propagation period takes about 8 months under greenhouse conditions maintaining day temperatures averaging from 20 to 22° C. and high humidity. Further growth then takes place under greenhouse conditions maintaining an average day temperature of 22° C., providing supplemental light for 18 hours during the winter at 40 W/m$^2$.

*Rooting description.*—Fine, well-branched, soft texture, and brown in color, RHS 200B.

Plant description:

*General appearance and form.*—Perennial fern plant with upright, rosette plant habit. In the center of the rosette, new fronds emerge as spiral structures. The center is hairy and brown, RHS 200B.

*Growth and branching habit.*—Fronds form from base.

*Growth rate/vigor.*—Slow growth rate, 1 cm per month, one new frond per every 3 weeks.

*Plant height* (*soil level to top of longest frond*).—About 20 cm.

*Plant width* (*spread*).—About 26 cm.

*Crop time to produce a mature flowering plant.*—After propagation, about 18 months are required to produce finished plants in 10.5 cm pots.

Foliage description:

*Arrangement.*—Very stiff, single fronds arranged as a rosette.

*Quantity per plant.*—About 35 fronds per plant.

*Longevity of cut fronds.*—Fronds have long vase life if cut.

*Length.*—Range from 5 to 20 cm. Middle fronds are the longest.

*Width.*—Range from 30 to 40 mm.

*Overall shape of leaf.*—Lanceolate.

*Shape at apex.*—Acuminate.

*Shape at base.*—Truncate.

*Margin.*—Wavy to curly.

*Strength.*—Crisp and very stiff.

*Texture.*—Smooth, glabrous, shiny.

*Color of developing foliage.*—Upper surfaces: Yellow-green, RHS 146A. Lower surface: Yellow-green, RHS 146B.

*Color of mature foliage.*—Upper surface: Yellow-green, RHS 147A. Lower surface: Yellow-green, RHS 147C.

*Venation pattern.*—Feather venation with thick central vein. Center veins are twisted.

*Venation color.*—Upper surface: Yellow-green, RHS 146C . Under surface: Yellow-green, RHS 146D, with a brown stripe, RHS 200B, extending 6 to 7 cm upward from the petiole, and fading to RHS 200A.

*Petiole length.*—About 2 to 3 cm.

*Petiole diameter.*—About 3 to 4 cm.

*Petiole texture.*—Very stiff.

*Texture.*—Smooth, glabrous, shiny.

*Petiole color.*—Yellow-green, RHS 146A, with a brown stripe, RHS 200A.

*Shape of center of plant.*—A rosette which is formed like a "bird's nest", from which fronds emerge, as initially spiral structures.

*Size of center of plant.*—About 2 cm in diameter.
*Color of center of plant.*—Brown, RHS 200B.
*Texture of center of plant.*—Hairy.

Sori:

*Number of sori per frond.*—About 100 to 150.
*Sori length.*—About 5 mm to 10 mm.
*Sori width.*—About 0.5 mm to 1.0 mm.
*Sori color.*—Grey-orange, RHS 176B.

Disease/pest resistance/susceptibility: Good resistance to diseases and pests common to *Aspleniums.*

Temperature tolerance: Plants of the new *Asplenium* 'CRISPY WAVE' have exhibited good tolerance to draught and rain. Low temperature tolerance to 2° C.

I claim:

1. A new and distinct cultivar of *Asplenium* plant named 'CRISPY WAVE', as illustrated and described herein.

* * * * *

'CRISPY WAVE'

'OSAKA'

'CRISPY WAVE'

'OSAKA'

'CRISPY WAVE'

'OSAKA'